United States Patent [19]

Mores et al.

[11] 4,066,789
[45] Jan. 3, 1978

[54] BLENDS OF LANOLIN WAX AND ESTERS OF ALIPHATIC POLYOLS AND FATTY ACIDS

[75] Inventors: Lee R. Mores, Cincinnati, Ohio; Justin P. McCarthy, Carteret; James J. Slack, Bound Brook, both of N.J.

[73] Assignee: Emery Industries, Inc., Cincinnati, Ohio

[21] Appl. No.: 666,432

[22] Filed: Mar. 12, 1976

[51] Int. Cl.$^2$ .................. A61K 7/00; A61K 47/00; A61K 7/027
[52] U.S. Cl. ......................................... 424/365; 106/9; 106/10; 106/28; 106/31; 106/245; 252/56 R; 424/64; 424/70
[58] Field of Search ............... 424/64, 365; 252/56 R, 252/9, 10; 106/28, 31, 245

[56] References Cited

U.S. PATENT DOCUMENTS

| | | | |
|---|---|---|---|
| 2,758,125 | 8/1956 | Sunde | 424/64 X |
| 3,210,248 | 10/1965 | Feldmann et al. | 424/365 |
| 3,658,555 | 4/1972 | Menz et al. | 424/365 X |
| 3,835,169 | 9/1974 | Kraft et al. | 424/365 X |
| 3,890,358 | 6/1975 | Hutchison et al. | 424/64 X |

*Primary Examiner*—Albert T. Meyers
*Assistant Examiner*—Vera C. Clarke
*Attorney, Agent, or Firm*—John D. Rice; Gerald A. Baracka

[57] ABSTRACT

Blends of the hard wax fraction obtained from the fractionation of lanolin and an ester derived from an aliphatic polyol or ether polyol and fatty acid are suitable substitutes for U.S.P. anhydrous lanolin and can be substituted therefore in cosmetic formulations (creams, lotions, etc.) without detracting from the properties of the system.

9 Claims, No Drawings

BLENDS OF LANOLIN WAX AND ESTERS OF ALIPHATIC POLYOLS AND FATTY ACIDS

BACKGROUND OF THE INVENTION

Lanolin (refined and neutralized wool grease) has a unique combination of emulsifying ability, emolliency and ability to absorb water which makes it extremely useful in a variety of cosmetic and pharmaceutical formulations. Numerous products such as hand, face and body creams and lotions, lipsticks and lip glosses, shampoos, hair preparations, body and both oils, make-ups, facial masks and suntan preparations utilize lanolin to impart desirable characteristics to the formulation. Lanolin is also useful in the textile industry as a softening agent and finds some use in industrial lubricating applications because of the anti-corrosive and rust preventive properties of the compound.

Anhydrous lanolin U.S.P. is described as a yellow, tenacious unctuous mass having a slight characteristic odor. It is insoluble in water but mixes without separation with about twice its weight of water. The product has a slight acid value and melts at about 36–42° C. Lanolin is a complex mixture of long-chain esters derived from higher alcohols, predominantly fused ring alcohols (sterols), and fatty acids and is one of the few natural fatty materials that contains a high percentage (~50%) of esterified hydroxy acids.

U.S.P. lanolin is not without some disadvantages in certain formulations. For example, a problem can arise due to incompatibility of the lanolin with hydrocarbon oils, the product may exhibit an undesirable amount of tackiness or emulsion stability may be unsatisfactory. For these reasons various derivatives of lanolin such as the ethoxylated and acylated derivatives have been developed. Lanolin can also be fractionated to obtain a more cosmetically elegant liquid form which has superior properties and improved compatibility with mineral oils. One such fractionation method utilizes a solvent crystallization process such as described in U.S. Pat. No. 2,758,125. Upon fractionation, in addition to obtaining the highly useful lanolin oil fraction, a solid fraction which is typically a hard waxy material melting at about 50° C is obtained. The high melting lanolin wax fraction has found some limited use in the cosmetic industry but because of its undesirable physical form it is more generally used in such products as shoe polishes, floor and furniture polishes, printing inks and carbon paper inks.

SUMMARY OF THE INVENTION

We have now quite unexpectedly found that the wax fraction obtained from the fractionation of lanolin can be modified by blending with commonly available esters and that the physical properties and performance characteristics of the resulting products closely resemble those of U.S.P. lanolin. By this invention it is possible to up-grade a material heretofore unacceptable for use in all but a few limited cosmetic formulations, and even then only at very low levels, to obtain a product suitable for general and widespread usage in the cosmetic industry as a lanolin substitute. While blending of two ester products is not unique, the results obtained in this instance are most surprising in view of the fact that the ester component is not derived from sterols or hydroxy acids but rather is obtained from conventional aliphatic polyols and aliphatic monocarboxylic (fatty) acids. In general, the products of this invention can be added to any formulation where U.S.P. lanolin is typically employed and these wax/ester blends can replace all or part of the U.S.P. lanolin in said formulation.

The advantages of this invention are numerous. In the first place, it is now possible to up-grade a hard, waxy intractable product which heretofore had limited usage so that it is acceptable for numerous additional large volume uses. Furthermore, the invention provides a relatively low cost, high quality lanolin substitute which is particularly desirable in view of the erratic availability of wool grease and the fluctuating price of lanolin. Still another feature of this invention is that it extends an animal product in short supply by the use of commonly available commercial esters. Additionally, this invention makes it possible to obtain more uniform product specifications or when desirable, to vary the physical characteristics of the end product within certain acceptable bounds by judicious selection of the ester and wax:ester ratio.

The compositions of this invention are obtained by melt-blending a hard lanolin wax fraction melting in the range 45°–60° C, and more generally 48–55° C, obtained from the fractionation of lanolin. The lanolin wax will generally have a saponification value between about 80 and 120 and a hydroxyl value of 20 to 40. The blends are prepared by melting the lanolin wax and blending therewith an ester or partial ester which is a liquid at 25° C or below and derived from an aliphatic polyol containing 2 to about 20 carbon atoms, or a condensation product thereof, and an aliphatic monocarboxylic acid containing from 8 to 20 carbon atoms. The ester component should have at least about 50%, and preferably greater than 75%, of the available hydroxyl groups esterified. Aliphatic polyols containing 3 to 12 carbon atoms and ether polyols derived therefrom having from 2 to 4 polyol units condensed are especially useful, particularly when the fatty acid moiety contains 14 to 18 carbon atoms. Esters and partial esters of glycerol, diglycerol and triglycerol and $C_{18}$ acids, particularly oleic acid and isostearic acid, are preferred for this invention. The blends will typically contain 30–70% by weight of the lanolin wax and 30–70 weight percent of the liquid ester or partial ester.

DETAILED DESCRIPTION

The present invention relates to the preparation of lanolin substitutes by blending the wax fraction obtained from the fractionation of lanolin with an ester derived from an aliphatic polyol and a fatty acid. The hard wax fraction is obtained from lanolin and separated from the light oil fraction by any one of a number of available fractionation procedures, however, the separation is generally accomplished using a solvent crystallization procedure such as described in U.S. Pat. No. 2,758,125 or a modification thereof. While the method by which the lanolin wax is obtained is not critical, useful wax fractions will melt in the range 45–60° C and, more preferably, from about 48° C to 55° C. Since the wax consists primarily of esters with some free alcohols it will generally have a saponification value between 80 and 120 and hydroxyl value between 20 and 40.

To obtain the useful products of this invention the lanolin wax is blended with an ester derived from an aliphatic polyol and an aliphatic monocarboxylic (fatty) acid. The term ester as used herein is intended to encompass both fully esterified products and partially esterfied products which contain both ester moieties

and hydroxyl (—OH) moieties within the molecule or where only a portion of the available hydroxyl functionality is reacted with the monocarboxylic acid. For the purpose of this invention, however, it has been found that when partial esters are employed at least about 50%, and more preferably greater than 75%, of the available hydroxyl groups should be esterified, i.e., be of the type

Additionally, the term ester also includes mixed ester products differing by virtue of the polyols and/or fatty acids from which they are derived or by virtue of the degree of esterification, i.e. a completely esterfied compound with a partial ester. Useful esters, particularly glycerides, can be derived from natural sources or they may be obtained employing conventional reaction procedures for the esterification of polyols and fatty acids.

Esters, naturally occurring or synthetic, useful for the present invention are derived from aliphatic polyols and aliphatic monocarboxylic acids and are liquids at about 25° C or lower, that is, have their solidification point at about 25° C or below. Ester products which are solids much above 25° C do not form acceptable blends with the lanolin wax. The aliphatic polyols from which the esters are derived can contain from about 2 to about 20 carbon atoms and, more preferably, from 3 to 12 carbon atoms. These polyols may be either straight-chain or branched and preferably contain no unsaturation. Useful aliphatic polyols include, for example, ethylene glycol, 1,2-propylene glycol, 1,3-propylene glycol, 1,2-butanediol, 1,3-butanediol, 1,4-butanediol, 1,5-pentanediol, 3-methyl-1,5-pentanediol, 2,3-dimethyl-2,3-butanediol, trimethylolpropane, glycerol, pentaerythritol, mannitol, sorbitol and the like. In addition to conventional aliphatic polyols, ether polyols (intermolecular ethers formed by the condensation of 2 or more polyol molecules accompanied by the elimination of water) can also be used. The ether polyols can contain 2 up to as many as 8 condensed polyol units, however, they will preferably contain 2 to 4 condensed polyol units. Illustrative ether polyols useful for this invention include diethylene glycol, triethylene glycol, tetraethylene glycol, diglycerol, triglycerol, tetraglycerol, pentaglycerol, hexaglycerol, heptaglycerol, octaglycerol, dipentaerythritol, tripentaerythritol, tetrapentaerythritol and the like. Superior blends are obtained when the lanolin wax is combined with complete or partial esters of aliphatic saturated polyols having 3 carbon atoms, such as glycerine and the propylene glycols, or condensation products thereof having 2 to 4 polyol units condensed. Esters of glycerol, diglycerol and triglycerol form a particularly useful embodiment of this invention and glycerol esters having at least 75% of the available hydroxyl functionality esterified, and even more preferably triglycerides, are especially preferred.

The aliphatic monocarboxylic acids from which the esters are derived will contain from about 8 to 20 carbon atoms, and more preferably, from about 14 to 18 carbon atoms. These acids can be alkyl-branched or straight-chain, contain either single or mutiple ethyleneic unsaturation and correspond to the formula R—COOH where R is an alkyl or alkenyl radical having 7-19, or preferably 13 to 17, carbon atoms. Aliphatic monocarboxylic acids containing 14 to 18 carbon atoms and which contain one or more lower alkyl groups ($C_{1-4}$) pendant to the chain and/or a single site of unsaturation within the molecule are particularly useful for this purpose. Esters derived from $C_{18}$ acids of the above type form a preferred embodiment of this invention with oleic acid and isostearic acid being especially useful in this regard.

A partial listing of liquid esters suitable for blending with the lanolin wax to obtain the useful products of this invention is provided and includes:

glycerol trioleate
glycerol dioleate
glycerol monooleate
glycerol triisostearate
glycerol diisostearate
glycerol monoisostearate
diglycerol diisostearate
diglycerol triisostearate
diglycerol trioleate
diglycerol tetraisostearate
triglycerol diisostearate
triglycerol triisostearate
triglycerol trioleate
sorbitan trioleate
dipropyleneglycol dipelargonte
dipropyleneglycol diisostearate
dipropyleneglycol dioleate
trimethylolpropane tripelargonate
trimethylolpropane triisostearate
trimethylolpropane trioleate The products of this invention are obtained by melt blending the lanolin wax with an appropriate amount of the ester. This can be accomplished using conventional procedures. Typically, the lanolin wax will be melted and the ester added thereto with stirring until a homogeneous blend is obtained. The mixture will then be allowed to cool to ambient conditions and will remain as a homogeneous mass for prolonged periods without separation of the components. The blends will generally contain from about 30–70% of the lanolin wax and 30–70% of the ester. Especially useful blends contain 40–60% lanolin wax and 40–60% by weight of the ester component.

While the properties of blends obtained in accordance with the present invention can vary depending on the particular wax component and ester component used and the ratio thereof, the blends are effective substitutes for lanolin and possess physical characteristics very similar to anhydrous U.S.P. lanolin even though a large portion of the blend (up to 70% in some cases) is made up of esters which are not derived from sterols or hydroxy acids. The present blends are a versatile cosmetic ingredient and can be freely substituted for lanolin, in whole or in part, in most cosmetic formulations without detracting from the stability, consistency and emolliency characteristics of the resulting formulation. These blends are compatible with most cosmetic formulations and form stable emulsions using conventional emulsion systems and procedures. Lotions and creams prepared with the lanolin substitutes of this invention cannot be distinquished in their physical appearance from those obtained using U.S.P. lanolin and the resulting formulations also have good application characteristics (spread easily without excessive drag). Neither do they impart an oily feel to the skin. Additionally, lipsticks and lip glosses prepared using these lanolin substitutes have good compatibility with dyes and lakes and form stable products which have good gloss and spread characteristics. Typically the product blends of this invention will have an acid value less than 5, water absorption greater than 200% and melt in the range 35°–50° C. Preferably, these compositions will have an acid value less than 2.5, a hydroxyl value less than 40, water absorption greater than about 350% and melt in the range 40°–47° C.

The following examples serve to illustrate this invention more fully, however, they are not intended as a limitation on the scope thereof. In these examples all parts and percentages are on a weight basis unless otherwise indicated.

EXAMPLE I

Equal parts by weight of the hard wax fraction obtained by the solvent crystallization of lanolin (Lanfrax ®, manufactured and sold by Malmstrom Chemicals, melting range 49°–52° C, saponification value 100, hydroxyl value 30) and glycerol trioleate (acid value 4, saponification value 195, pour point −15° C), the triglyceride of oleic acid comprising about 70–80% olive oil and also known as olein or triolein, were blended. Blending was accomplished by heating the wax above its melt point and blending in the glycerol trioleate with moderate agitation. When a homogeneous mass was obtained agitation was terminated and the product cooled to room temperature. Even after standing at ambient conditions for several months there was no evidence of phase separation. The wax/ester blend had approximately the same consistency and tack as U.S.P. lanolin with much improved color. The blend had an acid value of 1.86, Gardner color of about 5 (compared to a Gardner color of 9 for U.S.P. lanolin), water absorption of 480% (modified Griffen procedure) and melted at about 44.5° C.

To evaluate the emulsifiability of the wax/ester blend and characteristics of emulsions prepared therewith, cream formulations were prepared in accordance with the following recipe:

|  | Parts |
| --- | --- |
| Oil Phase |  |
| Beeswax (sunbleached) | 7 |
| Mineral Oil (70 SUS) | 50 |
| U.S.P. lanolin or wax/ester blend | 5 |
| Water Phase |  |
| Deionized water | 37 |
| Borax | 1 |

The emulsions were prepared by separately heating the oil and water phases to about 75° C, adding the water phase to the oil phase with stirring and cooling to 23° C with mixing. Behavior characteristics of the cream prepared using the wax/ester blend were very similar to those obtained with the U.S.P. lanolin-containing cream. Color was essentially identical as was thickness and application characteristics. Cream textures were not distinguishably different and the respective viscosities (measured at 3 rpm with a Brookfield Helipath Viscometer, Spindle TC) for the creams prepared with the wax/ester and U.S.P. lanolin were 20,000 cps and 18,600 cps. Emulsion stabilities of the two creams were essentially identical when stored at 120° F for two weeks.

To further demonstrate the ability of the wax/ester blend to be substituted for lanolin in cosmetics, lipsticks were prepared in accordance with the following formulation:

|  | Parts |
| --- | --- |
| Canadelilla Wax | 5.00 |
| Carnauba Wax | 2.00 |
| Ozokerite Wax | 1.50 |
| Spermaceti (Synthetic) | 1.50 |
| Myristyl Lactate | 4.00 |
| Mineral Oil (70 SUS) | 5.00 |
| Stabilizer | 0.20 |
| Beeswax (yellow) | 8.00 |
| 25% $TiO_2$ in Castor Oil | 32.00 |
| 25% Red No. 9 Barium Lake in Castor Oil | 6.00 |
| 25% Orange No. 17 Barium Lake in Castor Oil | 6.00 |
| 25% Red No. 21 in Castor Oil | 3.00 |
| Distilled Isopropyl Lanolate | 10.00 |
| Castor Oil | 3.80 |
| U.S.P. Lanolin or wax/ester blend | 12.00 |

All ingredients were combined, heated to about 85° C and stirred until homogeneous. The mixture was then poured into molds and allowed to cool. Sticks prepared using the wax/ester blend and U.S.P. lanolin were identical in color, feel, payoff and drag. The stick prepared with the wax/ester had a penetration value of 49.8 and the lanolin-containing stick had a penetration of 49.0. Both sticks had good gloss upon application and, after blotting, left about the same amount of color. Both sticks were stable at 120° F for at least four weeks and showed no signs of bleeding or sweating.

EXAMPLE II

The lanolin wax of Example I was blended with triglycerol diisostearate. Blend IIA contained equal parts of the wax and ester whereas blend IIB contained 70 parts lanolin wax and 30 parts of the triglycerol partial ester. Both wax/ester blends (acid values <2, iodine values <20) had approximately the same physical characteristics as U.S.P. lanolin with significantly improved color. Both products had melting points and viscosities comparable to the wax/ester blend of Example I but were slightly more tacky than that product. These blends were incorporated into the cream and lipstick formulations of Example I with no difficulty and the resulting products compared favorably with the control (prepared using U.S.P. anhydrous lanolin). Emulsion stability of the creams prepared using the lanolin wax/triglycerol diisostearate blend was also good. The wax/ester blends can also be used to replace all or a portion of the lanolin component in a typical body lotion formulation without detracting from the overall desirable characteristics of the lotion.

EXAMPLE III

A series of lanolin wax/ester blends were prepared using the lanolin wax product of Example I and following the above-described procedure. All blends contained equal parts of the wax and ester components. All of the resulting blends were comparable to U.S.P. anhydrous lanolin with slight variations with regard to consistency, color and tack. Beeswax/borax emulsions were prepared with these wax/ester blends in accordance with the formulation and procedure of Example I and the emulsions evaluated. The following table shows the ester component used for each blend and the viscosity of the resulting cream (measured with a Brookfield Helipath Viscometer, Spindle TB at 25° C and 3 rpm).

| Ester Component | Viscosity (cps) |
| --- | --- |
| Sorbitan trioleate | 568,000 |
| Dipropylene glycol pelargonate | 444,000 |
| Trimethylolpropane tripelargonate | 523,000 |
| Triglycerol triisostearate | 660,000 |

All of the emulsions were similar in physical appearance and consistency to the control emulsion prepared using U.S.P. lanolin even though the viscosity of the creams prepared from the sorbitan trioleate and triglycerol triisostearate were considerably higher than the viscosity of the lanolin-based cream. Viscosities can be lowered, however, by changing the wax/ester ratio or by substituting the wax/ester blend for only a portion of the lanolin. Emulsion stabilities (at 120° F) of the creams prepared with the wax/ester blends were essentially the same as obtained with the lanolin-based emulsion cream. Neither were there any significant differences in application and feel of these creams.

Lipsticks were also prepared from each of the blends using the lipstick formulation of Example I. While the sticks were slightly softer than obtained using U.S.P. lanolin or the wax/ester blend of Example I, they had comparable stability. No bleeding or sweating was apparent after two weeks at 120° F. The lipsticks had good application characteristics (spread, feel and gloss) and were comparable in all respects to the lanolin-based stick.

EXAMPLE IV

Fifty parts glycerol monoisostearate were blended with 50 parts of the hard wax fraction (m.P. about 50° C) obtained from the solvent crystallization of lanolin. The homogeneous blend had an acid value of 0.92, iodine value of 15.7 and melted at 44.5° C. the blend was similar in appearance, texture, and consistency to anhydrous lanolin U.S.P. and had significantly improved color (Gardner color 5). The lanolin wax/glycerol monoisostearate blend formed stable beeswax/borax emulsions and was readily substituted for lanolin in a variety of useful cosmetic creams and lotions. The wax/ester blend could be substituted for all or part of lanolin without detracting from the desirable characteristics of the formulations. Similarly, when the wax/ester blend was incorporated into the lipstick formulation of Example I a stick having good characteristics was obtained. While the stick exhibited a slightly darker shade than obtained using U.S.P. lanolin, it was not distinquishable in drag and payoff characteristics. The stick was stable at 120° F for at least four weeks and showed no indication of bleeding or sweating.

We claim:

1. A composition useful as a substitute for anhydrous lanolin U.S.P. consisting essentially of:
   a. a hard wax fraction obtained from the fractionation of lanolin and melting in the range of 45°-60° C; and
   b. an ester or partial ester of an aliphatic polyol containing from 2 to 20 carbon atoms or an ether polyol obtained by the condensation of from 2 to 8 of said aliphatic polyol units and an aliphatic monocarboxylic acid containing from about 8 to 20 carbon atoms, said ester or partial ester being a liquid at 25° C or lower; and said composition containing from about 30 to 70% by weight of component (a) and 30-70 weight percent of component (b).

2. The composition of claim 1 wherein the partial ester has at least 50% of the available hydroxyl groups esterified.

3. The composition of claim 1 having an acid value less than 5, water absorption greater than 200% melting in the range 33°-50° C.

4. The composition of claim 1 wherein component (a) melts in the range of 48°-55° C and component (b) is derived from a monocarboxylic acid containing 14 to 18 carbon atoms and an aliphatic polyol containing 3 to 12 carbon atoms or an ether polyol thereof having 2 to 4 polyol units.

5. The composition of claim 4 wherein component (a) has a saponification value between 80 and 120 and hydroxyl value from about 20 to 40 and component (b) is glycerol, diglycerol or triglycerol having at least 75% of the available hydroxyl functionality esterified with a $C_{18}$ monocarboxylic acid.

6. The composition of claim 5 wherein the $C_{18}$ monocarboxylic acid is oleic acid.

7. The composition of claim 5 wherein the $C_{18}$ monocarboxylic acid is isostearic acid.

8. The composition of claim 5 containing 40-60 weight percent of component (a) and 40-60 weight percent of component (b).

9. The composition of claim 8 having an acid value less than 2.5, a hydroxyl value less than 40 and melting in the range 40°-47° C and wherein component (b) is gylcerol trioleate.

* * * * *

UNITED STATES PATENT AND TRADEMARK OFFICE
CERTIFICATE OF CORRECTION

PATENT NO. : 4,066,789
DATED : January 3, 1978
INVENTOR(S) : Lee R. Mores, Justin P. McCarthy, James J. Slack It is certified that error appears in the above-identified patent and that said Letters Patent are hereby corrected as shown below:

Column 1, line 12, "both" should read ---bath---.
Column 4, line 30, "dipelargonte" should ---dipelargonate---.
Column 5, line 37, "1,86" should read ---1.86---.
Column 7, line 37, "m.P."should read ---m.p.---.

Claim 3, line 2, after "200%" should be inserted ---and---.
Claim 3, line 3, "33°" should read ---35°---.

*Signed and Sealed this*

*Twenty-seventh* Day of *June 1978*

[SEAL]

Attest:

RUTH C. MASON
*Attesting Officer*

DONALD W. BANNER
*Commissioner of Patents and Trademarks*